US011273221B2

(12) United States Patent
Fleury et al.

(10) Patent No.: US 11,273,221 B2
(45) Date of Patent: Mar. 15, 2022

(54) TRANSLOCATION OF SYNTHETIC POLYMERS BY LIPID MEMBRANES (71) Applicant: FORSCHUNGSZENTRUM JUELICH GMBH, Juelich (DE)

(72) Inventors: Jean Baptiste Fleury, Saarbruecken (DE); Juergen Allgaier, Aachen (DE); Gerald Schneider, Baton Rouge, LA (US)

(73) Assignee: FORSCHUNGSZENTRUM JUELICH GMBH, Juelich (DE)

( * ) Notice: Subject to any disclaimer, the term of this patent is extended or adjusted under 35 U.S.C. 154(b) by 24 days.

(21) Appl. No.: 16/337,477

(22) PCT Filed: Oct. 6, 2017

(86) PCT No.: PCT/EP2017/075496
§ 371 (c)(1),
(2) Date: Mar. 28, 2019

(87) PCT Pub. No.: WO2018/065583
PCT Pub. Date: Apr. 12, 2018

(65) Prior Publication Data
US 2019/0262454 A1 Aug. 29, 2019

(30) Foreign Application Priority Data
Oct. 7, 2016 (DE) .......................... 102016119102.7

(51) Int. Cl.
*A61K 47/10* (2017.01)
*A61K 47/12* (2006.01)
*A61K 47/34* (2017.01)

(52) U.S. Cl.
CPC .............. *A61K 47/10* (2013.01); *A61K 47/12* (2013.01); *A61K 47/34* (2013.01)

(58) Field of Classification Search
CPC ......... A61K 47/10; A61K 47/12; A61K 47/34
See application file for complete search history.

(56) References Cited

U.S. PATENT DOCUMENTS

| 5,702,717 | A | 12/1997 | Cha |
| 5,998,588 | A | 12/1999 | Hoffman |
| 2002/0013252 | A1 | 1/2002 | Schmiedel |
| 2002/0015734 | A1 | 2/2002 | Uludag |
| 2003/0232961 | A1* | 12/2003 | Manias |
| 2005/0025820 | A1 | 2/2005 | Kester |
| 2005/0277739 | A1 | 12/2005 | Yang |
| 2007/0224241 | A1 | 9/2007 | Stayton |
| 2012/0177592 | A1 | 7/2012 | Radosz |
| 2012/0225027 | A1* | 9/2012 | Extner |
| 2017/0151334 | A1 | 6/2017 | Maeder |
| 2019/0110497 | A1* | 4/2019 | Liu |

FOREIGN PATENT DOCUMENTS

| JP | H11513985 A | 11/1999 |
| JP | 2006524707 A | 11/2006 |
| JP | 2008502785 A | 1/2008 |
| WO | 9709068 A1 | 3/1997 |
| WO | 9715287 A1 | 5/1997 |
| WO | 0140429 A1 | 6/2001 |
| WO | 0170288 A2 | 9/2001 |
| WO | 2004096140 A2 | 11/2004 |
| WO | 2005121196 A1 | 12/2005 |
| WO | 2007109584 A1 | 9/2007 |
| WO | 2008150996 A1 | 12/2008 |
| WO | 20150161841 A2 | 10/2015 |

OTHER PUBLICATIONS

Kumar (Journal of the American Chemical Society, published 2004, pp. 10640-10644) (Year: 2004).*
Quesnel (Molecules, pp. 98-104, Published 2005) (Year: 2005).*
Guo et al. (Applied Materials & Interfaces, Published Jul. 20, 2012, pp. 4006-4014) (Year: 2012).*
Bray (Macromolecules, published 2010, pp. 9426-9433) (Year: 2010).*
Werner et al., Biomacromolecules, 2015, 16, pp. 125-135.
Bayley et al., Molecular BioSystems, vol. 4, No. 12, Dec. 2008, pp. 1191-1208.

* cited by examiner

*Primary Examiner* — Alma Pipic
(74) *Attorney, Agent, or Firm* — Abel Schillinger, LLP (57) ABSTRACT

The present invention relates to a copolymer containing alternating hydrophobic and hydrophilic units and to the use of said copolymers as carrier for active ingredients through a lipid bilayer, especially a lipid membrane.

20 Claims, 1 Drawing Sheet

TRANSLOCATION OF SYNTHETIC POLYMERS BY LIPID MEMBRANES

BACKGROUND OF THE INVENTION

1. Field of the Invention

The present invention relates to a copolymer containing alternating hydrophobic and hydrophilic units and to the use of said copolymers as carrier for active ingredients through a lipid bilayer, especially a lipid membrane.

2. Discussion of Background Information

Copolymers which are used in medicine and can pass through a partition membrane must be biocompatible. WO 2015/161841 A2 discloses modified poly(dicarboxylic acid multiol esters) for controlled active-ingredient release, which esters are biocompatible as implantable carrier systems. In said systems, active ingredients are covalently bonded to free hydroxyl groups of the copolymer. Werner et al (Biomacromolecules, 2015, 16, 125-135) simulates amphiphilic copolymers on the basis of mathematical models and attempts to theoretically predict the properties thereof with regard to absorption and passive translocation at or through a lipid-bilayer membrane. The finding was that the copolymers should have a lipophilic character with HLB values between 5 and 10. In addition, Werner et al. does not describe the chemical structure of the simulated copolymers.

Within the context of the invention, the term "translocation" through a lipid-bilayer membrane is used to mean penetration of said membrane, preferably by means of passive transport, i.e., the relocation of molecules, especially copolymers, from one side of said membrane to the other, regardless of the mechanism.

As described by Werner et al., there are a few substances known at present which penetrate into cells by means of translocation, including, for example, so-called CPP (cell-penetrating peptides) and polyelectrolytes. As further carrier systems for controlled release, WO 2015/161841 mentions, for example, non-water-soluble microparticles and nanoparticles. Block copolymers, random copolymers or gradient copolymers are, for example, disclosed by DE 69 620 898 T2, WO 01/70288 A2, WO 2005/121196 A1 or WO 2007/109584 A1. Carrier molecules for, for example, anti-cancer active ingredients are also disclosed by WO 2008/150996 A1. However, translocation is not attributed to these carriers.

The aim of these carrier systems for controlled active-ingredient release (also called drug carrier systems) is, firstly, to prevent a rapid excretion of active ingredients from the body. Most conventional active ingredients are small and therefore stay for only a short period in the circulation, since they are below the renal threshold owing to their size, and are therefore separated from the blood and excreted.

Secondly, it is intended that, as far as possible, the carrier systems transport the active ingredients in a specific manner into the proximity of certain organs or cells and release them there in as controlled a manner as possible.

SUMMARY OF THE INVENTION

It is an object of the present invention to provide carriers which allow translocation through a lipid bilayer, i.e., a lipid-bilayer membrane, especially a cell membrane, and do not have the disadvantages of the prior art—such as, for example, nanotoxicity or undesired interactions owing to the ionic character of the molecules with cellular components. Furthermore, said molecules are also to be able to transfer or transport non-membrane-crossable active ingredients and agents having a biological effect into cells. In one embodiment, the cell membrane is not to be damaged at the same time. In addition, the copolymers according to the invention are to be soluble in aqueous medium for use of said copolymers under physiological conditions.

This object is achieved by a copolymer covalently or physically connected to at least one active ingredient and containing or consisting of a main chain containing alternating hydrophobic and hydrophilic units, characterized in that the copolymer has an LCST value of from 20° C. to 90° C., 20° C. to 80° C., 20° C. to 70° C., preferably 25° C. to 90° C. and in particular 25° C. to 90° C. or 35° C. to 90° C.

The main chain is the polymerization product, possibly condensation or addition product, of the at least two monomers which form the copolymer and is substantially linear, preferably linear.

According to the invention, the LCST value describes the lower critical solution temperature, i.e., below said LCST value, the copolymers according to the invention are completely soluble in water or aqueous solutions. At temperatures above the LCST value, the polymers become insoluble.

LCST can be determined by means of turbidimetry or by means of differential scanning calorimetry.

Alternatively, the LCST value is determined visually; in this case, the LSCT value is that temperature at which turbidity arises in the solution. Said turbidity is caused by the precipitation of the polymers.

In one alternative, the polymers do not have an exact, isolated LCST value, but have instead an LCST range. According to the invention, the LCST values and/or especially in the case of LCST ranges concern a temperature interval around the determined value of 30 or 20% of the particular value, preferably of 15% and in particular 10%. This means that an LCST value determined, for example, to be 20° C. also includes values of from 14 to 26 degrees Celsius or 16 to 24 degrees Celsius, preferably 17 to 23 degrees Celsius and in particular 18 to 22 degrees Celsius.

Completely soluble means that the copolymers according to the invention are dissolved in a molecularly dispersed manner, i.e., form a real solution. In this context, the term "aqueous solution" is used for solutions which can contain not only water as solvent, but also further substances dissolved in a molecularly dispersed manner, such as salt ions for example. In view of body fluids, aqueous solutions also contain further substances which can be present in suspended or dispensed form.

The polymers according to the invention consist of alternating hydrophilic and hydrophobic units. Within the context of the invention, the individual units of the hydrophobically/hydrophilically alternating copolymers according to the invention are not identical to the monomers used as starting material; in particular, the hydrophilic or hydrophobic character of the units of the polymers according to the invention is not identical in all embodiments to the hydrophilic or hydrophobic character of the monomers used as starting materials.

According to the invention, a hydrophobic unit and/or group is a unit and/or group which reduces the LCST value of a polymer. This can be determined by a simple comparison: first of all, the LCST value of a synthesized or starting polymer is determined. Thereafter, a derivative of said polymer that contains a further unit and/or group is synthesized. Alternatively, such a unit and/or group is incorporated into the starting polymer. Thereafter, the LCST value of this second polymer is determined. If the second measured LCST value is lower than the first, a hydrophobic unit is concerned, and if the second measured LCST value is higher than the first, a hydrophilic unit is concerned. Thus, the LCST value is a measure of the hydrophilicity or hydrophobicity of a polymer.

An example of a hydrophilic unit is EO or, as starting material, PEG. Examples of hydrophobic units or starting materials are polyalkanediol, polypropylene glycol, polybutylene glycol and/or polytetramethylene glycol for alcohols.

For example, glutaric acid can be used to produce polymers according to the invention, even though it is highly water-soluble at 640 g/L at 20° C. Glutarates, as present in polyesters, are, however, substantially hydrophobic and, at most, slightly water-soluble. For example, the solubility of dimethyl glutarate in water is only 53 g/L. What is significant is the solubility behavior of the polymer in water.

The polymers according to the invention have a lower critical solution temperature (LCST). Below the LCST, the polymers are soluble, and above, they are insoluble. Via molecular weights of the starting materials of the hydrophilic and hydrophobic units and via their molecular-weight ratio, it is possible to set the LCST. In addition, the polarity of the components is significant. For example, the more nonpolar the starting material of the hydrophobic units, the lower the molecular weight thereof for setting a given LCST. (See Table 1: P(EG4PG3) vs. P(C4EG4); in the case of P(C5EG4), an LCST value of 13° C. was determined). In addition, the nature of the bond formed in the polymerization reaction is significant. Ester bonds are nonpolar and thus enlarge the hydrophobic units. Amide or urethane bonds are polar and thus enlarge the hydrophilic units.

A particular advantage of the copolymers according to the invention is their good water solubility under physiological conditions, especially at temperatures between 25° C. and 50° C., preferably 25° C. to 45° C. or 30° C. to 50° C.

The copolymers are hydrophilic on the basis of their LCST values and therefore have an overall hydrophilic character, i.e., they are water-soluble at room temperature. Within the context of the invention, "alternating hydrophobic and hydrophilic units" means that there are alternating copolymers in which the hydrophobic and hydrophilic units are alternately present: -abababab-. For example, a symbolizes a hydrophobic unit and b a hydrophilic unit, or vice versa.

Therefore, these alternating copolymers differ from, for example, random copolymers, in which the distribution of the two units in the chain is random, such as, for example, -aaabbababbbbaababaa-. Also different are gradient copolymers, which are similar to the random copolymers, but in which the proportion of one unit increases over the course of the chain, whereas the proportion of the other unit decreases, such as, for example, -aaaabaaabbaabbbabbbb. Block copolymers and segment copolymers differ, too, in structure from the alternating copolymers according to the invention, since longer sequences or blocks composed of the hydrophobic and hydrophilic units in each case are present here.

The copolymers according to the invention therefore have a ratio of hydrophilic to hydrophobic units of substantially 1:1, with regard to the term "substantially" therefore a deviation of not more than 10% in each case, i.e., a ratio of 1.1:0.9 to 0.9:1.1; preferably 1:1. Deviations may arise in particular when one of the two monomer units is used in excess in the synthesis, with the result that said monomer unit preferentially forms the chain ends.

In one alternative, the hydrophilic units (EO-)l or derivatives such as, for example, polyether dicarboxylic acids (as also described below) have a higher molecular weight than the hydrophobic units and/or the hydrophobic starting materials.

In a further embodiment, the copolymers according to the invention are characterized by their molar masses, especially by a number-average molar mass $M_n$ of from 1000 to 100 000 g/mol, preferably 2000 to 50 000, 2500 to 25 000, particularly preferably 3000 to 14 000 g/mol, from 3200 to 13 000, and in particular 3500 to 12 000 g/mol. In one alternative, the number-average molar mass $M_n$ is from 1000 to 20 000, preferably from 1000 to 10 000 and in particular 1000 to 5000 or 1000 to 3000 g/mol. In another alternative, the number-average molar mass $M_n$ is from 7000 to 14 000, preferably from 8000 to 13 000 and in particular 7500 to 12 000 g/mol or a molecular-weight range from at least 5000 to below 10 000, i.e., $5000 < M_n < 10\ 000$.

According to the formula A: $D = M_w/M_n$, what arises is a polydispersity D for the copolymers according to the invention of from 1.01 to 3.0, preferably 1.3 to 2.0, determined by means of appropriate GPC methods.

Preferably, the copolymers according to the invention have a value D of 1.01-1.6, in particular 1.3-1.6.

In one alternative, for fractionated polymers, D is from 1.01 to 1.2 or 1.01 to 1.5, preferably 1.01 to 1.3, particularly preferably 1.01 to 1.2 and in particular 1.01 to 1.17 or 1.01 to 1.15. According to the invention, fractionated means a separation according to molecular weight, i.e., there are fractions with a narrow molecular-weight distribution.

In one embodiment, the copolymers according to the invention are present as discrete molecules, i.e., they are not crosslinked and/or do not form gels either.

In one alternative, the particular building blocks, i.e., monomer building blocks, therefore the hydrophobic and/or hydrophilic units, are building blocks with a narrow molecular-weight distribution. This means that the reactants used likewise have a narrow molecular-weight distribution, preferably a polydispersity D as specified above. The building blocks can also have a defined molar mass and molecular structure, for example dicarboxylic acids such as succinic acid or adipic acid.

In one embodiment, the copolymer according to the invention is characterized in that it contains or consists of a substantially linear main chain.

According to the invention, the term "substantially linear" describes a molecule having a linear main chain which determines the length of the copolymer. The copolymers according to the invention can optionally have branches, but are constructed from bifunctional monomeric building blocks which optionally have short branches ui side chains. This means that at the linear main chain, which constitutes the base, can have side chains. In one alternative, the side chains are—under physiological conditions—inert radicals such as, for example, alkyl, aryl or alkylaryl radicals. In a further alternative, some side chains, the polymer ends or additional side chains or all are provided with terminal, functional groups for binding active ingredients. In this case, either the copolymers or the active ingredients contain a complementary functional group A which reacts with the complementary functional group B which is present in the other reaction partner. The complementary functional group A and B are selected from the group containing or consisting of:

| A and B and | B or A |
|---|---|
| —SH | —C(O)—OH |
| —NH₂ | —C(O)—O—C(O)— |
| —OH | —NCO |
| —O—(CO)—NH—(CO)—NH₂ | —NH—C(O)—OR |
| —O—(CO)—NH₂ | —CH₂—OH |
| >NH | —CH₂—O—R |
|  | —NH—CH₂—O—R |
|  | —NH—CH₂—OH |
|  | —N(—CH₂—O—R)₂ |
|  | —NH—C(O)—CH(—C(O)OR)₂ |
|  | —NH—C(O)—CH(—C(O)OR)-(—C(O)—R) |
|  | —NH—C(O)—NR¹R² |
|  | >Si(OR)₂ |
|  | 1,2-epoxyethyl |
| —C(O)—OH | 1,2-epoxyethyl |
|  | —N=C=N— |
|  | —C(O)—N(CH₂—CH₂—OH)₂ |
| ethylene group (vinyl groups) | ethylene group |

In one embodiment, the copolymers according to the invention are not the reaction product of a radical polymerization. In one alternative, the copolymers according to the invention do not contain double bonds for further crosslinking.

In a further embodiment, the copolymers according to the invention contain or consist of at least two hydrophilic and two hydrophobic units, preferably 3 hydrophilic units and 3 hydrophobic units, particularly preferably 5 hydrophilic units and 5 hydrophobic units and in particular 10 hydrophilic units and 10 hydrophobic units.

In one embodiment, the copolymer is substantially nonionic. According to the invention, the term "substantially nonionic" describes a molecule which is aqueously soluble owing to its hydrophilic character and not owing to an ionic character. The copolymers can have terminal end groups and/or side groups which are present as ions depending on the pH. However, these do not influence aqueous solubility.

In a preferred embodiment, the hydrophilic unit of the copolymers is defined by the formula (I)

—(CH2-CH2-O-)$l$ where $l$=2 to 30 or 2 to 20, preferably 2 to 18 or 2-16.

One embodiment of the present invention concerns copolymers where $l$=3-20, preferably 3-10 and in particular 4-6.

The copolymer according to the invention is therefore, in one alternative, characterized in that at least four and preferably at least six ether functions and/or derivatives thereof are present in the main chain.

Within the context of the invention, an ether function is a functional group, i.e., an ether group of the general formula R1-O—Ra, where Ra= or R1=CH2-CH2 or R1 and/or Ra is, independently of one another, a radical having a C3 to C10 hydrocarbon chain. The radical can be linear or branched or contain or consist of aromatics.

In a further embodiment, the copolymer is characterized in that at least two and preferably at least four further functions are present in the main chain, selected from the group containing or consisting of ester, amide and/or urethane functions and/or derivatives and/or combinations thereof.

A further embodiment of the present invention concerns the copolymer according to the invention that is a condensation product from dicarboxylic acids and diols and therefore has at least 2 and preferably at least 4 ester functions and/or derivatives thereof in the main chain.

Within the context of the invention, an ester function is a functional group, i.e., an ester group of the general formula R2COOR3. Therefore, the monomers of the copolymer according to the invention are linked together in the main chain via ester groups.

The copolymer according to the invention with ester function is described by the general formula II:

(~R2-CO—O—R3-O—CO-)$n$;

where n=3-500, preferably 3-100, wherein the specified Mw values are not exceeded, and
where R2 and R3, independently of one another, contain or consist of 1 to 60 (owing to in each case 30 EO units) carbon atoms and optionally contain at least one oxygen atom in the main chain between two carbon atoms.

R2 is the dicarboxylic acid radical and R3 is the diol radical. The radical can be linear or branched or contain or consist of aromatics.

The dicarboxylic acid has 4-12 carbon atoms, preferably 4-8 and particularly preferably 4-6.

In one embodiment, R2 and/or R3 contains or consists of at least one hydrophilic unit according to formula I.

In one alternative, the copolymer according to the invention is therefore the condensation product from dicarboxylic acid of the formula II-1a: HOOC—R2-COOH with a polyethylene glycol (PEG),
of the formula II-1b: HO-(EO-)$l$-H, R2 and $l$ as described above. E represents CH2-CH2, i.e., two CH2 groups, EO therefore represents ethoxy.

If R2 contains at least 10 carbon atoms, preferably as a chain, R3 is constructed from not more than 20 EO units.

Preference is given to using PEG with a molecular weight of 150-1000 g/mol, preferably approx. 150 to 600 g/mol and in particular 200 to 450 or 200 to 300 g/mol. In this alternative, R3 is a radical composed of 2-30 EO groups, preferably 4-20 and particularly preferably 6-14, 4-10 or 4-6.

In a further alternative, the copolymer according to the invention is the condensation product of a polyethylene glycol dicarboxylic acid of the formula II-2a:

HOOC—CH2-O-(EO-)($l$-2)-CH2-O—COOH with a diol of the formula II-2b:

HO—(CH2)$n1$-OH.

n1=2-20, preferably 2-10 and particularly preferably 2-8, 2-6 or 2-4.

In one embodiment, the copolymer according to the invention has at least two and preferably four functions in the main chain that are not an ester function.

Within the context of the invention, these functions are, in one alternative, amide functions. An amide function is a functional group, i.e., an amide of the formula R4-CO—NRb2-R5. This means that an amide function is the product of a condensation of a carboxylic acid with an amine.

Rb is, independently of one another, H, —CH3, —CH2CH3, —CH2CH2CH3, —CH2CH2CH2CH3, preferably methyl, alkyls having C4-C8-chains, aryls (preferably phenyl or naphthyl), alkylaryls (preferably benzyl) or other inert radicals, particularly preferably H, methyl or ethyl and in particular H or methyl.

Therefore, the monomers of the copolymer are linked together via amide functions.

The copolymer according to the invention with amide function is described by the general formula III:

—(R4-CO—NR$b$-R5-NR$b$-CO-)$m$;

m=5-500, preferably 5-100, wherein the specified Mw values are not exceeded, and R4 is the dicarboxylic acid radical and R5 is the diamine radical. The radical can be linear or branched or contain or consist of aromatics.

In one embodiment, R4 and/or R5 contains or consists of, by way of example, at least one hydrophilic unit according to formula I.

In one alternative, the copolymer according to the invention is therefore the condensation product from dicarboxylic acid of the formula III-1a (identical to II-1a):

HOOC—R4-COOH with a polyethylene glycol diamine,
of the formula III-1b:

H2N-CH2-CH2-O-(EO-)($l$-2)-CH2-CH2-NH2.

In this alternative, R4 is an alkyl composed of 2-12 methylene groups, preferably 4-8 and particularly preferably 4-6.

In a further alternative, the copolymer according to the invention is the condensation product of a polyethylene glycol dicarboxylic acid of the formula III-2a (identical to II-2a):

HOOC—CH2-(EO-)($l$-2)-CH2-COOH with a diamine of the formula III-2b:

H2N-(CH2)$m1$-NH2, and m1=2-20, preferably 2-10 or 4-12 and particularly preferably 2-8 or 4-6.

In a further alternative, the copolymer contains at least two and preferably four urethane functions in the main chain. A urethane function within the context of the invention is a functional group, i.e., a urethane group of the formula R6-NH—CO—O—R7, i.e., the addition product of an isocyanate with an alcohol. Therefore, in this alternative, the monomers in the main chain are linked together by urethane functions.

The copolymer according to the invention with urethane function is described by the general formula IV:

—(R6-NR$b$-CO—O—R7-O—CO—NR$b$-)$o$;

o=5-500, preferably 5-100, wherein the specified Mw values are not exceeded, and R6 is the diisocyanate radical and R7 is the diol radical. The radical can be linear or branched or contain or consist of aromatics.

In one embodiment, R6 and/or R7 contains or consists of at least one hydrophilic unit according to formula I.

In one alternative, the copolymer according to the invention is therefore the addition product from diisocyanate of the formula IV-1a:

O═C═N—R6-N═C═O with a polyalkoxydiol, preferably polyethylene glycol, of the formula IV-1b (identical to formula I):

HO-(EO-)$l$-H, as described above.

Preference is given to using PEG with a molecular weight of 150-1000 g/mol, preferably approx. 150 to 600 g/mol and in particular 200 to 450 or 200 to 300 g/mol. In this alternative, R6 is an alkyl composed of 2-10 methylene groups, preferably 4-8 and particularly preferably 4-6.

In a further alternative, the copolymer according to the invention is the addition product of a polyethylene glycol diisocyanate of the formula IV-2a:

O═C═N—(CH2)$n4$-(EO-)$l$-(CH2)$n5$-N═C═O with a diol of the formula IV-2b (identical to II-2b):

HO—(CH2)$n3$-OH, where
n4=n5=2-20, preferably 2-10, particularly preferably 2-8 and in particular 2;
n3=2-20, preferably 2-10 and in particular 2-8.

A further embodiment of the present invention concerns the copolymer according to the invention that is a condensation product from diols and therefore has at least 2 and preferably at least 4 ether functions and/or derivatives thereof in the main chain. Within the context of the invention, an ether function is a functional group, i.e., an ether group of the general formula (V) R8-O—R9. Therefore, the monomers of the copolymers according to the invention are linked together in the main chain via ether groups.

The copolymers according to the invention with ether functions are produced by using, as starting materials, diols which, on their part, are preferably polyethers selected from the group containing or consisting of polyethylene glycol, polypropylene glycol, polybutylene glycol, polytetramethylene glycol, polyalkanediol and polyethers constructed from alkoxy units having 5 and more carbon atoms.

Preference is given to using the copolymers according to the invention from hydrophilic starting materials such as polyethylene glycol and hydrophobic diols such as, for example, polypropylene glycol, polybutylene glycol, polytetramethylene glycol, polyalkanediol and polyethers constructed from alkoxy units having 5 and more carbon atoms.

In one embodiment, R8 and/or R9 contains or consists of at least one hydrophilic unit according to formula I. R8 and/or R9 can be linear or branched or contain or consist of aromatics.

In preferred embodiments, the copolymers are polyethers or polyesters, particularly polyesters, as described. The functional end groups can bind active ingredients.

Further preferred embodiments are:

In one embodiment, the starting materials used for the hydrophilic units are preferably polyethylene glycol or polyethylene glycol derivatives, especially selected from the group containing or consisting of:
polyethylene glycol (HO—(CH2-CH2-O)$l$-H), polyethylene glycol bis(carboxymethyl) ether (HOOC—CH2-O—(CH2-CH2-O)($l$-2)CH2-COOH), polyethylene glycol diethylamine (H2N-(CH2-CH2-O-)($l$-2)CH2-CH2-NH2) and polyethylene glycol bis(isocyanatomethyl) ether (OCN—CH2-O—(CH2-CH2-O-)($l$-2)CH2-NCO).

In a further embodiment, the starting materials used for the hydrophobic units are hydrocarbon radicals bearing two terminal functional groups, preferably selected from the group:
alkanediol (HO—(CH2)p-OH), alkanedicarboxylic acid (HOOC—(CH2)(p-2)-COOH), alkanediamine (H2N-(CH2)(p-2)-NH2) and alkane diisocyanate (OCN—(CH2)(p-2)-NCO), where p=1-20, preferably 1-12.

The hydrocarbon radical (CH2)p can be linear or else branched. In addition, the hydrocarbon radical can include functional groups as described above, i.e., complementary functional group A or B.

In a further embodiment, the copolymers according to the invention are the reaction product of a so-called Michael addition. This involves linking hydrophobic and hydrophilic units via carbon-carbon single bonds, carbon-sulfur bonds, carbon-oxygen bonds or carbon-nitrogen bonds. Michael addition is the addition of a so-called Michael donor to an alpha,beta-unsaturated carbonyl compound referred to as Michael acceptor. Michael acceptor acceptors are, for example, alpha,beta-unsaturated aldehydes, ketone esters or carboxylic amides or alpha,beta-unsaturated nitriles. Michael donors which are used are compounds which are nucleophilic and preferably relatively soft in accordance with HSAB theory, such as, for example, compounds which form, as a result of addition of a base, in the alpha-position anions, i.e., deprotonated carbonyl compounds. Amines, thiols, phenolate ions or cyanides can be used as such nucleophiles. What are used as reactants for the copolymers according to the invention are compounds which have, in each case, two functional groups for a Michael addition, i.e., either two Michael acceptors, two Michael donors, or a Michael acceptor and a Michael donor. In the reactants or at least one reactant, an EO-(I) chain can be present between the two functional groups (Michael acceptor, Michael donor). Especially suitable as Michael acceptors are polyethylene glycol dimethacrylates or polyethylene glycol diacrylates (polyethylene glycol esterified at both chain ends with methacrylic acid or acrylic acid). Especially suitable as Michael donor are alkanedithiols such as 1,4-butanedithiol or 1,6-hexanedithiol.

Starting materials which can also be used for the hydrophobic units are hydrophobic polymers, provided that they bear functional end groups. Particularly suitable are polyethers such as polypropylene glycol, polybutylene glycol or polytetrahydrofuran. The end groups can be alcohols, amines or else other functional groups.

By means of suitable polymerization methods, what are produced from the starting materials of the hydrophilic or hydrophobic units are the polymers consisting of alternatingly hydrophilic and hydrophobic units. Suitable polymerization methods are, for example, polycondensation or polyaddition. What are obtained as a result are, for example, polyesters, polyamides, polyethers or polyurethanes.

For example, the polymerization of a polyethylene glycol with a dicarboxylic acid leads to a polyester of the structure —(OC—(CH2)p-2-CO—O(CH2-CH2-O)l)x-. Alternatively, the polyester can also be obtained by reaction of a polyethylene glycol bis(carboxymethyl) ether with an alkanediol.

What is obtained by reacting a polyethylene glycol bis(carboxymethyl) ether with an alkanediamine is a polyamide having the following structure; —(OC—CH2-O—(CH2-CH2-O-)l-CH2-CO—(NH)—(CH2)p2-(NH))x-, where x defines the number of repeat units and arises from the above-described molar mass.

As an alternative to the abovementioned compounds, it is also possible to use other compounds in order to increase reactivity. For example, a carboxylic acid group can be converted into an acid chloride in order to produce therefrom a polyester or a polyamide. To produce polyethers from, for example, a polyethylene glycol and a diol, one of the two components can be converted in an intermediary manner to form the corresponding ditosylate in order to then produce the polyether having the following structure: —(O—(CH2-CH2-O)l-(CH2)p2)x-.

Instead of primary amines, it is also possible to use secondary amines. In this case, preference is given to methylated amines having, for example, the structure H(CH3)N—(CH2)(p-2)-N(CH3)H.

The end groups of the polymer chains arise from the starting materials used. In a polyester, carboxylic acid and alcohol groups appear, for example. The end groups have no significant influence on the translocation behavior of the polymers. The end groups can also be modified by postpolymerization reactions in order, for example, to bind active-ingredient molecules.

Also possible, instead of linear chains, are branched structures, which, for example, can be obtained by using mixtures of difunctional and trifunctional starting materials. However, the proportion of starting material which is more than difunctional must be sufficiently low for a soluble polymer to be always obtained.

The starting materials of the hydrophilic and hydrophobic units can be monodisperse. However, they can also have a molecular-weight distribution. This applies in particular to polymeric starting materials. Low-molecular-weight starting materials, such as dicarboxylic acids, can, too, be used as mixtures of different chain lengths.

The present invention also provides a method for producing the above-described copolymers.

An advantage of the method according to the invention is the simple preparation of the copolymers, which, in one alternative, are immediately usable without further workup.

In another alternative, a workup can be effected, especially purification of the polymers.

In this case, it is possible, through differing solubility of the polymers, to separate and purify certain fractions with a relatively narrow molar-mass distribution.

For the separation, all the polymers are preferably dissolved in water or some other solvent and, through addition of nonsolvents, the relevant copolymer fractions are precipitated according to their solubility. This separation method is temperature-dependent.

The separation can also be achieved by a change in temperature.

As a result, low- and high-molecular-weight fractions are separated. This corresponds to fractionation, see the examples.

According to the invention, the molecular weights, both Mw and Mn, of the copolymers can be determined by means of gel permationgraphy, optionally coupled with online light-scattering detection (GPC-LS), or NMR by means of end-group determination.

Furthermore, within the context of the invention, the proportions of OH and COOH end groups are ascertained via 1H-MNR to calculate the molecular weight (Mn).

The present invention also provides a copolymer, as described above, for use as carrier for active ingredients, i.e., agents having a biological effect. The copolymer serves as carrier for active ingredients, agents having a biological effect, since said copolymer allows translocation through a lipid-bilayer membrane, preferably a cell membrane, for these substances, i.e., brings about and allows in the first place the translocation of the substances.

Within the context of the invention, active ingredients or agents having a biological effect are to be used identically. In one embodiment, active ingredients are medicinal products as defined in the Arzneimittel-Gesetz [German medicinal products act] section 2 (1) and section 2 (2) as well as section 4 (19) as of Apr. 4, 2016. In one alternative, active ingredients are to be understood to mean all substances having a pharmaceutical and/or biological effect. Active ingredients are therefore compounds selected from the group consisting of pharmaceutically active compounds, therapeutically effective compounds and biologically active compounds, cosmetically active compounds, substances which influence biochemical and/or physiological processes in an organism and/or in a quantitative manner, i.e., promote them, allow them in the first place or inhibit them.

Furthermore, active ingredients develop, in small amounts, a large pharmaceutical, chemical, biological or physiological effect.

In one embodiment, active ingredients are also dyes, fluorescent labels, radioactive labels.

In a further embodiment, active ingredients or agents having a biological effect are also biocides.

In one embodiment, the above-described copolymers do not have any further functional groups in addition to the above-described ester functions and OH and COOH end groups. Correspondingly, in one embodiment, the above-described copolymers, as condensation product of dicarboxylic acids with amines and addition product of isocyanates with diols, do not have any further functional groups in addition to the amide functions or urethane functions and the COOH and NH2 end groups or OH end groups.

In a further alternative, the above-described copolymers have functional groups. Functional groups are above-described radicals or molecules which are covalently bonded to the copolymers. Functional groups can be introduced in order to modify the chemical and physical properties of the copolymers or in order to bind active ingredients, agents having a biological effect, thereto.

The invention therefore provides the above-described copolymers connected or linked to the active ingredient, wherein the linkage is a covalent bond.

In a further embodiment, the present invention provides the above-described copolymers linked to an active ingredient, wherein the linkage is not a covalent bond.

In this case, the linkage is achieved via hydrogen bonds, hydrophilic, hydrophobic or electrostatic interaction or bond and/or steric immobilization. Compared to covalent linkage, a noncovalent linkage offers simpler release of the active ingredients, since there is no need to cleave a chemical bond; instead, just changes in the physical environment can lead to release.

In one alternative, noncovalent linkage can be achieved by enclosing active ingredients in the superstructure of the above-described copolymers.

The present invention also provides the above-described copolymer linked to an active ingredient, or to an agent having a biological effect, for use as medicament. The invention further provides for the use of the above-described copolymer as carrier for active ingredients and agents having a biological effect for transport through a lipid-bilayer membrane, especially a cell membrane.

The invention also provides for the use of the above-described copolymer linked to an active ingredient and/or agent having a biological effect as medicament.

Formulation is achieved by methods known to a person skilled in the art, as described, for example, in Arzneiformellehre [formulation theory], 4th edition, by Ursula Schöffling 2003.

In one embodiment, the above-described copolymers are, however, used and employed ex vivo for, for example as above-described carrier, testing the translocation of different active ingredients in vitro. To this end, what are done are tests carried out as described in the examples. In particular, an artificial lipid-bilayer membrane is suitable for this purpose.

According to the invention, the copolymers and active ingredients are tailored to one another. For example, if there is a hydrophobic active ingredient with a high molecular weight, it is connected to a copolymer with a higher molecular weight and/or with a higher LCST value. An overall strong hydrophilic character of the copolymer linked to the active ingredient is therefore achieved.

In one embodiment, different copolymers—with regard to the chemical composition of the starting materials or with regard to the molecular weight—are used with possibly different active ingredients in order to thus ensure translocation of an active ingredient over a relatively long period or in order to ensure an exact sequence of different active ingredients.

The present invention also provides a kit containing the above-described copolymers. In one alternative, such a kit contains the above-described copolymers in solution. In another alternative, they are in powder form. Furthermore, a kit can, for example, contain receptacles containing buffers or solutions. All the components can be packaged in the same receptacle or separately from one another. Furthermore, it is also possible for instructions for the use of the kit to be present. The copolymers can, for example, be present in an induction bottle with plug or septum. In addition, the kit can also contain a disposable syringe for collecting the samples.

The above-described copolymers and the corresponding production method offer the possibility of producing precisely tailored copolymers, especially with regard to their hydrophobic and hydrophilic properties and LCST values. For example, since the amide and/or urethane functions are more polar than the ester functions, it is possible to incorporate hydrophobic elements, such as CH2 chains for example, between these functions in order to achieve a higher hydrophobic portion.

BRIEF DESCRIPTION OF THE DRAWINGS

In the accompanying drawings.

DETAILED DESCRIPTION OF EMBODIMENTS OF THE INVENTION

Examples

1. Production of the Polymers According to the Invention

P(C4EG6): 16.81 g of succinic anhydride (168 mmol) was mixed in a glass flask with 49.97 g of polyethylene glycol 300 (Mn=298 g/mol, 168 mmol) and 53 mg of toluenesulfonic acid monohydrate and heated to 120° C. under argon for one day with stirring. Thereafter, the pressure was lowered to 100 mbar and heating to 160° C. was carried out within 2 hours. At this temperature, the pressure was lowered further to 20 mbar. After 16 hours, the pressure was reduced further to approx. 0.1 mbar and heating was carried out for a further 4 days. The product thus obtained was used further without further workup.

P(C5EG6): 12.91 g of glutaric acid (97.5 mmol) was mixed in a glass flask with 29.01 g of polyethylene glycol 300 (Mn=298 g/mol, 97.4 mmol) and 37 mg of toluenesulfonic acid monohydrate and heated and stirred under vacuum conditions (approx. 0.1 mbar). Heating was carried out to 80° C., 100° C. and 120° C., for one hour in each case. Thereafter, the temperature was increased to 140° C. for 3 hours and heating was lastly carried out at 160° C. for 62 hours. The product thus obtained was used further without further workup.

P(C6EG6): 24.24 g of adipic acid (166 mmol) was mixed in a glass flask with 49.54 g of polyethylene glycol 300 (Mn=298 g/mol, 166 mmol) and 58 mg of toluenesulfonic acid monohydrate and heated and stirred at 100 mbar. Heating was carried out to 120° C., 140° C. and 160° C., for one hour in each case. Thereafter, the pressure lowered to 50 mbar and heated further at 160° C. for 16 hours. At this temperature, the pressure was reduced to approx. 0.1 mbar within one day and the mixture was left for 4 further days under these conditions. The product thus obtained was used further without further workup.

P(C4EG4): 32.58 g of succinic anhydride (326 mmol) was mixed in a glass flask with 63.21 g of tetraethylene glycol (325 mmol), 351 mg of toluenesulfonic acid monohydrate and 117 g of toluene and heated to boiling point with stirring at reflux with interconnection of a water separator. After 2 days, the pressure was lowered to approx. 0.1 mbar and the mixture was heated at 120° C. for one further day. The product thus obtained was used further without further workup.

P(C8EG13): 15.53 g of suberic acid (89.2 mmol) was mixed in a glass flask with 53.40 g of polyethylene glycol 600 (Mn=599 g/mol, 89.1 mmol) and 70 mg of toluenesulfonic acid monohydrate and heated and stirred at 100 mbar. Heating was carried out to 120° C., 140° C. and 160° C., for one hour in each case. Thereafter, the pressure lowered to 10 mbar and heated further at 160° C. for 16 hours. At this temperature, the pressure was reduced to approx. 0.1 mbar within one day and the mixture was left for 2 further days under these conditions. The product thus obtained was used further without further workup.

P(C10EG22): 15.16 g of sebacic acid (75.0 mmol) was mixed in a glass flask with 73.95 g of polyethylene glycol 1000 (Mn=986 g/mol, 75.0 mmol), 85 mg of toluenesulfonic acid monohydrate and 112 g of toluene and heated to boiling point with stirring at reflux with interconnection of a water separator. After one day, the pressure was lowered to approx. 0.1 mbar and the mixture was heated at 140° C. for 5 further days. The product thus obtained was used further without further workup.

P(EG4PG3): 33.16 g of poly(ethylene glycol) bis(carboxymethyl) ether (Mn=217 g/mol, 153 mmol) was mixed in a glass flask with 29.38 g of tripropylene glycol (153 mmol) and 110 mg of toluenesulfonic acid monohydrate and heated and stirred to 120° C. at 100 mbar for half an hour. Thereafter, the pressure was reduced to 5 mbar at 140° C. within 3.5 hours. After a further 18 hours, the temperature was increased to 160° C. and stirring was then additionally carried out for 2 days at 5 mbar and for one day at approx. 0.1 mbar. The product thus obtained was used further without further workup.

Fractionation of P(C5EG6): 7.35 g of P(C5EG6) were dissolved in 500 mL of toluene and 1.4 L of ethanol were added slowly at room temperature with stirring until the mixture was distinctly cloudy. Through gentle heating, a clear solution was obtained, which was cooled back to room temperature over several hours. After the lower phase which formed as a result had settled, the clear, supernatant mixture was decanted off, admixed with further ethanol, heated until the mixture became clear, cooled slowly to room temperature, and the clear, supernatant liquid was separated from the second lower phase. This process was repeated twice more. Altogether, 3.3 L of ethanol were added. The 4 lower phases were dried, washed with ethanol and lastly dried in order to obtain the fractions P(C5EG6)-F1 to P(C5EG6)-F4. The polymer still dissolved in the toluene/ethanol mixture was isolated by distilling off the solvents and dissolved in 1 L of ethanol at 70° C. By means of stepwise cooling, what were obtained between 39° C. and −15° C. were 4 further fractions, which were dried (fractions P(C5EG6)-F5 to P(C5EG6)-F8). Each of the fractions comprised between around 0.5 g to 1 g of polymer.

Example 2: Characterization of the Polymers

Absolute molecular weights (number-average molecular weight Mn and weight-average molecular weight Mw beforehand) and the polydispersity Mw/Mn of the polymer products were ascertained by means of gel permeation chromatography, coupled with online light-scattering detection (GPC-LS), in THF as mobile solvent. Mn and the proportions of OH and COOH end groups (% OH, % COOH) were ascertained via 1H-NMR in deuterated pyridine. The polydispersity Mw/Mn was additionally ascertained via GPC with PEO calibration (GPC-PEO). In this case, a mobile-solvent mixture composed of 84% by weight of THF, 15% by weight of dimethylacetamide and 1% by weight of acetic acid was used. The results are outlined in Table 1.

Nonfractionated copolymers have a broad molecular-weight distribution. Since low-molecular-weight fractions are not completely captured by means of GPC-LS, these values are somewhat below the values determined by means of GPC-PEO.

TABLE 1:

| | | GPC-LS | | NMR | | GPC-PEO | | Trans- |
|---|---|---|---|---|---|---|---|---|
| | LCST | Mn | Mw/Mn | % OH | % COOH | Mn | Mw/Mn | location |
| P(C5EG6) | 42° C. | 11700 | 1.51 | 34 | 66 | 12000 | 2.46 | + |
| P(C4EG6) | 64° C. | 6590 | 1.58 | 62 | 38 | 5340 | 1.97 | + |
| P(C6EG6) | 28° C. | 8700 | 1.59 | 53 | 47 | 7750 | 2.20 | + |
| P(C5EG14) | 83° C. | 6390 | 1.52 | 67 | 33 | 5210 | 2.23 | + |
| P(C8EG13) | 47° C. | 3780 | 1.52 | 58 | 42 | 3070 | 2.00 | + |
| P(C4EG4) | 29° C. | 5160 | 1.38 | 45 | 55 | 8230 | 2.58 | + |
| P(C10EG22) | 35° C. | 10100 | 1.49 | 59 | 41 | 9750 | 1.65 | − |
| P(EG4PG3) | 21° C. | 20100 | 1.63 | | | | | |
| P(C5EG6)-F1 | | 34400 | 1.16 | | | | | + |
| P(C5EG6)-F2 | | 25100 | 1.08 | | | | | + |
| P(C5EG6)-F3 | | 16600 | 1.07 | | | | | + |
| P(C5EG6)-F4 | | 12900 | 1.05 | | | | | |
| P(C5EG6)-F5 | | 9300 | 1.07 | 33 | 67 | 11600 | | + |
| P(C5EG6)-F6 | | 6400 | 1.07 | | | | | + |
| P(C5EG6)-F7 | | 4200 | 1.12 | | | | | + |
| P(C5EG6)-F8 | | 2290 | 1.15 | | | | | + |

According to the nomenclature used above, P represents a polymer which is a copolymer polyester. The acid unit is defined at the first position; this contains, for example, a chain composed of z4 carbon atoms for C4, 5 carbon atoms for C5 (C5 is HOOC—(CH2)3-COOH), etc. The alcohol unit is defined at the second position and contains, for example, a chain composed of 6 condensed ethylene glycol subunits for EG6 and a chain composed of 14 condensed ethylene glycol subunits for EG14, etc. If, at the first position, EG4 represents the dicarboxylic acid for example, the starting material is a polyethylene glycol dicarboxylic acid based on an ethylene glycol having 4 approx. EO units, with the terminal carbon atoms being present in carboxyl groups.

Example 3: Ascertainment of the Membrane-Crossability of the Polymers

The membrane-crossability of the polymers according to the invention, i.e., the translocation through a membrane, was determined by using a variant of the so-called droplet interface bilayer DIB method according to Bayley of 2008 in Journal Anal Chem. According to said method, a free-standing lipid-bilayer membrane was generated in a microfluidic chip.

The microchannels of the chips were arranged such that they intersect. The microchannels were first filled with a phospholipid mixture (DOPC, 1,2-dioleoyl-sn-glycero-3-phosphocholine) dissolved in squalene.

At two opposing ends, an aqueous phase containing 100 mM NaCl was injected into two ends of the channels by means of a volume-controlled pump for injection syringes.

The aqueous phase from the syringes formed two so-called fingers or bubbles, which enlarge away from the injection syringes. After a few seconds, what was formed in both cases at the phase boundary between water phase and oil phase was a lipid monolayer which extended over the entire finger. Upon mutual contacting of the two fingers containing the lipid monolayer, a lipid bilayer was formed from these two lipid monolayers. This process was not done immediately, but on the basis of the drawback or the channeling-away of the oil, in this case the squalene, between the two lipid monolayers during a so-called "zipping process". After its formation, the bilayer was stable and could be analyzed simultaneously by optical microscopy and by electrophysiological experiments.

The polymers according to the invention were dispersed or dissolved in the aqueous phase in one of the syringes, meaning that the polymers according to the invention were present in one of the fingers, whereas they were not in the other finger. The latter contained only the aqueous 100 mM NaCl solution in pure water (e.g., distilled water or demineralized water).

Thus, the polymers according to the invention were only present on one side of the phospholipid-bilayer membrane formed. After 24 hours, samples (approx. 100 to 200 μl using a micropipette) were collected from the aqueous phase which originally did not contain the polymers according to the invention and chemically analyzed.

Samples from multiple microfluidic chips or multiple experiments were first collected until there was approx. an amount of one milliliter.

The chemical analysis of the aqueous samples was carried out as follows:

The water was removed by freeze-drying. The residues obtained were characterized by means of GPC and 1H-NMR. As comparison or control, the original solution containing the polymers according to the invention that was injected on one side was likewise chemically analyzed in this manner.

For the copolymers according to the invention: P(C5EG6), P(C4EG6), P(C6EG6)P and (C8EG13), GPC chromatograms and NMR spectra of the control were identical to those of the collected samples.

Determination of Permeation Kinetics by Means of Osmometry:

As described above, the lipid bilayer was formed by contact of two water drops in an oil phase. The two so-called water fingers were injected into microchannels by means of a pressure-controlled system. The pressure-controlled system consisted of a hydrostatic reservoir which was directly connected to the microchannel. The two water fingers were therefore pushed toward one another by both sides of the microchannel system until they contacted one another and thus formed the lipid bilayer. At the same time, the continuous oil phase, which was originally in the microchannels, was displaced. After contact of the two drops, or in this case the water fingers, and the formation of the lipid bilayer that is based thereon, a mechanical equilibrium arose, since the pressure acting on the two water fingers was equalized. The hydrostatic pressure which acted on each of the two water fingers is precisely set by the level of the water reservoir (Ph=p×g×h). One of the two water drops (water fingers) was pure aqueous buffer solution, whereas the other contained the polymers according to the invention in a concentration of approx. 5 mg/ml in the same buffer. Owing to the translocation through the lipid bilayer, the polymer concentration in the two water fingers changed over time and the mechanical equilibrium thereby broke down. On its part, this brought about again a very slow shift of the lipid bilayer within the microchannel. The location of the lipid bilayer was precisely recorded using a microscope. The position of the lipid bilayer was reset by changing the pressure on a water finger, specifically by changing the level of the water reservoir. The change in hydrostatic pressure necessary for restoring the equilibrium of the bilayer directly expressed the change in osmotic pressure caused by the change in polymer concentration.

As reference material, polyethylene glycol having a molecular weight of Mn=2000 g/mol was used.

Figure 1:
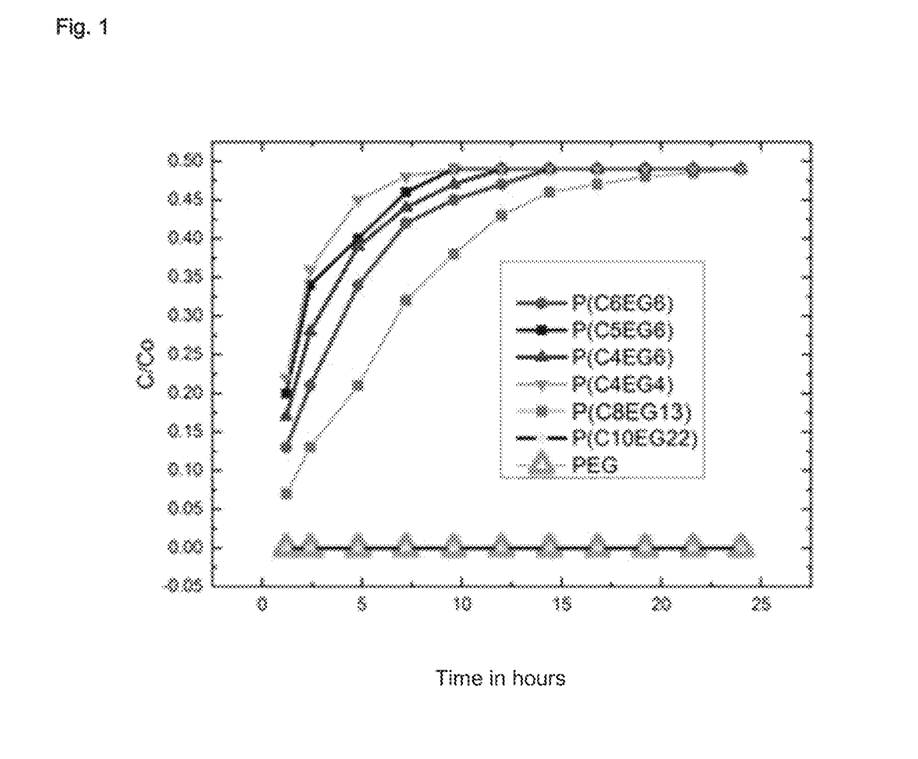
FIG. 1 and FIG. 2 show diagrams representing the translocation kinetics of the synthetic polymers described in the Examples.
Figure 2:
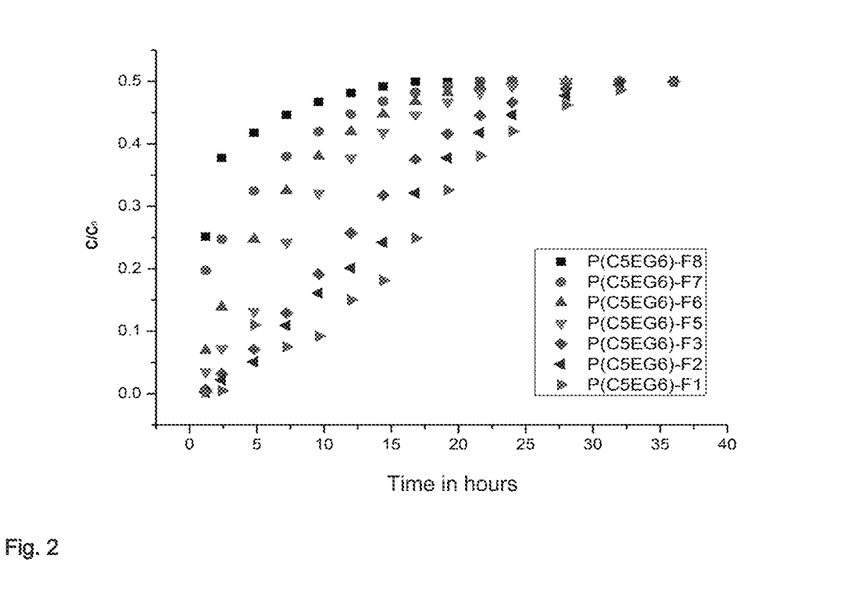

FIGS. 1 and 2 show the translocation kinetics measured by means of osmometry. The C/Co value of 0 at the start of measurement means that all polymer is situated on one membrane side. A value of 0.5 means that the polymer concentration is identical on both sides of the membrane.

In FIG. 1, the values for PEG and P(C10EG22) overlap.

It is clear therefrom that translocation of the copolymers through the bilayer membrane has taken place.

What is claimed is:

1. A copolymer, wherein the copolymer is covalently or physically connected to at least one active ingredient, consists of alternating hydrophobic and hydrophilic units, consists of a substantially linear main chain, is substantially nonionic, has a number-average molecular mass Mn of from 2,000 to 50,000 g/mol, and has a Lower Critical Solution Temperature (LCST) of from 20° C. to 90° C., the hydrophilic units of the copolymer being of the formula —(CH2-CH2-O-)l, where l=3 to 20, and the starting materials for the hydrophobic units being selected from alkane dicarboxylic acids of formula HOOC—$(CH_2)_p$—COOH, alkane diamines of formula $H_2N$—$(CH_2)_p$—$NH_2$, and alkane diisocyanates of formula OCN—$(CH_2)_p$—NCO, where p=2 to 20.

2. The copolymer of claim 1, wherein the copolymer has an LCST of from 20° C. to 80° C.

3. The copolymer of claim 1, wherein the copolymer has an LCST of from 20° C. to 70° C.

4. The copolymer of claim 1, wherein the copolymer has a number-average molecular mass Mn of from 2,500 to 25,000 g/mol.

5. The copolymer of claim 1, wherein a ratio of hydrophilic to hydrophobic units is from 1.1:0.9 to 0.9:1.1.

6. The copolymer of claim 1, wherein the at least one active ingredient is selected from pharmaceutically active compounds, therapeutically effective compounds, cosmetically active compounds, and substances which influence biochemical and/or physiological processes in an organism.

7. The copolymer of claim 1, wherein the at least one active ingredient is selected from dyes, fluorescent labels, and radioactive labels.

8. The copolymer of claim 1, wherein l=3 to 8.

9. The copolymer of claim 1, wherein l=4 to 6.

10. The copolymer of claim 1, wherein at least four ether functions are present in a main chain thereof.

11. The copolymer of claim 1, wherein at least six ether functions are present in a main chain thereof.

12. The copolymer of claim 1, wherein at least four functions selected from ester, amide and/or urethane functions and/or derivatives and/or combinations thereof are present in a main chain thereof.

13. The copolymer of claim 1, wherein the copolymer has a number-average molecular mass Mn of from 3,000 to 14,000 g/mol.

14. The copolymer of claim 1, wherein the copolymer has a Mw/Mn of from 1.01 to 1.6.

15. The copolymer of claim 1, wherein the copolymer has a Mw/Mn of from 1.3 to 1.6.

16. The copolymer of claim 1, wherein the copolymer is capable of carrying the at least active ingredient through a lipid bilayer.

17. The copolymer of claim 16, wherein the lipid bilayer is a part of a biological membrane.

18. The copolymer of claim 1, wherein p=2 to 12.

19. The copolymer of claim 1, wherein the copolymer is a part of a medicament.

20. A method for the transport of an active ingredient through a lipid bilayer, wherein the method comprises providing the copolymer of claim 1 in an aqueous solution on one side of the lipid bilayer.

* * * * *